United States Patent [19]

Davidowicz et al.

[11] Patent Number: 5,121,642
[45] Date of Patent: Jun. 16, 1992

[54] LIQUID SAMPLING METHOD AND APPARATUS

[75] Inventors: Joseph Davidowicz, Williamson; Alan R. Bentz, Bergen, both of N.Y.

[73] Assignee: Eastman Kodak Company, Rochester, N.Y.

[21] Appl. No.: 629,874

[22] Filed: Dec. 19, 1990

[51] Int. Cl.$^5$ .............................................. B01L 3/02
[52] U.S. Cl. ............................... 73/864.11; 73/864.01
[58] Field of Search .......... 73/864.02, 864.11, 864.15, 73/863.32, 440

[56] References Cited

U.S. PATENT DOCUMENTS

| | | | |
|---|---|---|---|
| 2,396,470 | 3/1946 | Mortensen | 73/33 |
| 2,959,964 | 11/1960 | Streitfeld | 73/864.16 |
| 3,451,273 | 6/1969 | Ludlow | 73/440 |
| 3,465,595 | 3/1969 | Tansony | 73/421 |
| 4,046,011 | 9/1977 | Olsen | 73/421 |
| 4,248,830 | 2/1981 | Kallies et al. | 73/864.11 |
| 4,271,704 | 6/1981 | Peters | 73/864 |
| 4,900,515 | 2/1990 | Miramanda | 73/864.02 |

Primary Examiner—Hezron E. Williams
Assistant Examiner—Howard Wisnia
Attorney, Agent, or Firm—L. George Legg

[57] ABSTRACT

An apparatus and method for sampling liquids is disclosed. The apparatus includes a pipet having a chamber, a first opening at one end for introducing liquid into the chamber, and a second opening at the other end for introducing or removing a gas for respectively pressurizing or depressurizing the chamber. Positioned in the chamber is a freely movable first sealing member having a specific gravity greater than the specific gravity of the liquid and a first seat, for cooperatively containing a sample of liquid in the chamber. Also positioned in the chamber is a freely movable second sealing member having a specific gravity less than the specific gravity of the liquid and a second seat, for cooperatively limiting further flow of liquid into the chamber once a sample is obtained. Equipment for introducing or removing a gas is also provided.

13 Claims, 2 Drawing Sheets

LIQUID SAMPLING METHOD AND APPARATUS

FIELD OF THE INVENTION

This invention relates to apparatus and methods for sampling liquids. More particularly, it relates to such apparatus and methods for taking discrete liquid samples of a predetermined volume or amount, and to taking such samples remotely or at selected depths in a vessel containing the sampled liquid.

BACKGROUND OF THE INVENTION

Fluid testing and fluid sampling apparatus and methods are known in the prior art and have been used for many years. Although fluid testing apparatus such as disclosed in U.S. Pat. No. 2,396,470 may suffice for the purpose of testing a sample of a liquid, such fluid testing apparatus is awkward and is difficult to use for obtaining and containing a sample of a liquid.

Some prior art fluid sampling devices, such as a syringe, have had the disadvantage of requiring visual monitoring and direct control and handling while obtaining the sample, which is undesirable for many applications. Examples of such applications include taking submersed samples from a volume of liquid, and sampling where operator proximity to the sampled liquid should be minimized as in sampling hazardous liquids.

Other sampling devices comprising elastomeric valve materials such as rubber may not sufficiently withstand corrosive or other hostile liquid environments, which severely limits the range of applications of such devices. Another problem with some prior art sampling devices is that they may require pumping the sample to a transport container instead of retaining the sample within the sampling chamber, which may be undesirable in some applications. For example, in sampling a two-phase system such as a photographic emulsion it is desirable to obtain the sample with the phases representative and unchanged or undisturbed by such pumping and transport operations.

There are many situations where it is desired to sample a fluid at a predetermined depth, but with prior art sampling devices it can be difficult to control and verify at what depth the sample is being drawn. Thus, the operator may not be able to adjust the sampling apparatus to accommodate various sampled liquids, sampling depths, and sampling time. Another problem is that the sample can tend to leak out of the sampling container.

Still another problem with known sampling devices and methods is that they may allow the drawing of one discreet sample but not be conducive to the concurrent drawing of multiple samples by one operator or by one operation or step. For example, it may be desirable to obtain concurrent samples to determine, for example, whether a liquid is well-mixed or stratified. Such sampling devices and methods may also not allow the operator to control the rate at which a sample is drawn or the volume of sample obtained. Such liquid samplers may also not be convenient to use in obtaining multiple samples in a dark environment, for example as is necessary in photographic manufacturing processes.

RELATED ART

U.S. Pat. No. 2,396,470 discloses a fluid testing method and apparatus. The apparatus comprises a pipet having a chamber within which two beads are positioned and retained. One bead has a specific gravity less than, and one bead a specific gravity more than, the specific gravity of the tested fluid. First and second stop means are provided adjacent the ends of the chamber for receiving and retaining the beads.

U.S. Pat. No. 3,465,595 discloses a liquid sampling device comprising a container having a one-way check valve in a liquid inlet opening. The check valve comprises an elastomeric material having a flattened or duckbill portion that is limitedly expansible under hydrostatic pressure to admit liquid to the container and that is collapsible under the influence of air pressure within the container to seal the inlet. The apex of the cover of the container is provided with an air vent for venting air displaced from the container by entering liquid and also for pumping air into the container.

U.S. Pat. No. 4,046,011 discloses a sampling device having a one-way check valve at the liquid inlet, an air vent, and an outlet line to remove liquid samples to a sample container. The check valve comprises a concave shaped member constructed of a soft pliable material such as rubber. Hydrostatic pressure lifts the valve from its seat so that fluid can flow into a sampling chamber, and air pressure within the chamber collapses the valve to seal the inlet. A pulse relay operator controls the flow of air to the chamber to direct the sampling and sample removal cycle.

U.S. Pat. No. 4,271,704 discloses a method of sampling a fluid and a fluid sampling device comprising a hollow body having an interior chamber and having a conical sampling passage and a control passage. A sample valve in the sampling passage comprises a valve seat with a freely movable spherical or ball valve member having a specific gravity less than the specific gravity of the sampled liquid. A control valve, such as an automobile tire valve, is positioned in the control passage to permit the chamber to be pressurized.

SUMMARY OF THE INVENTION

Figures 1, 2:
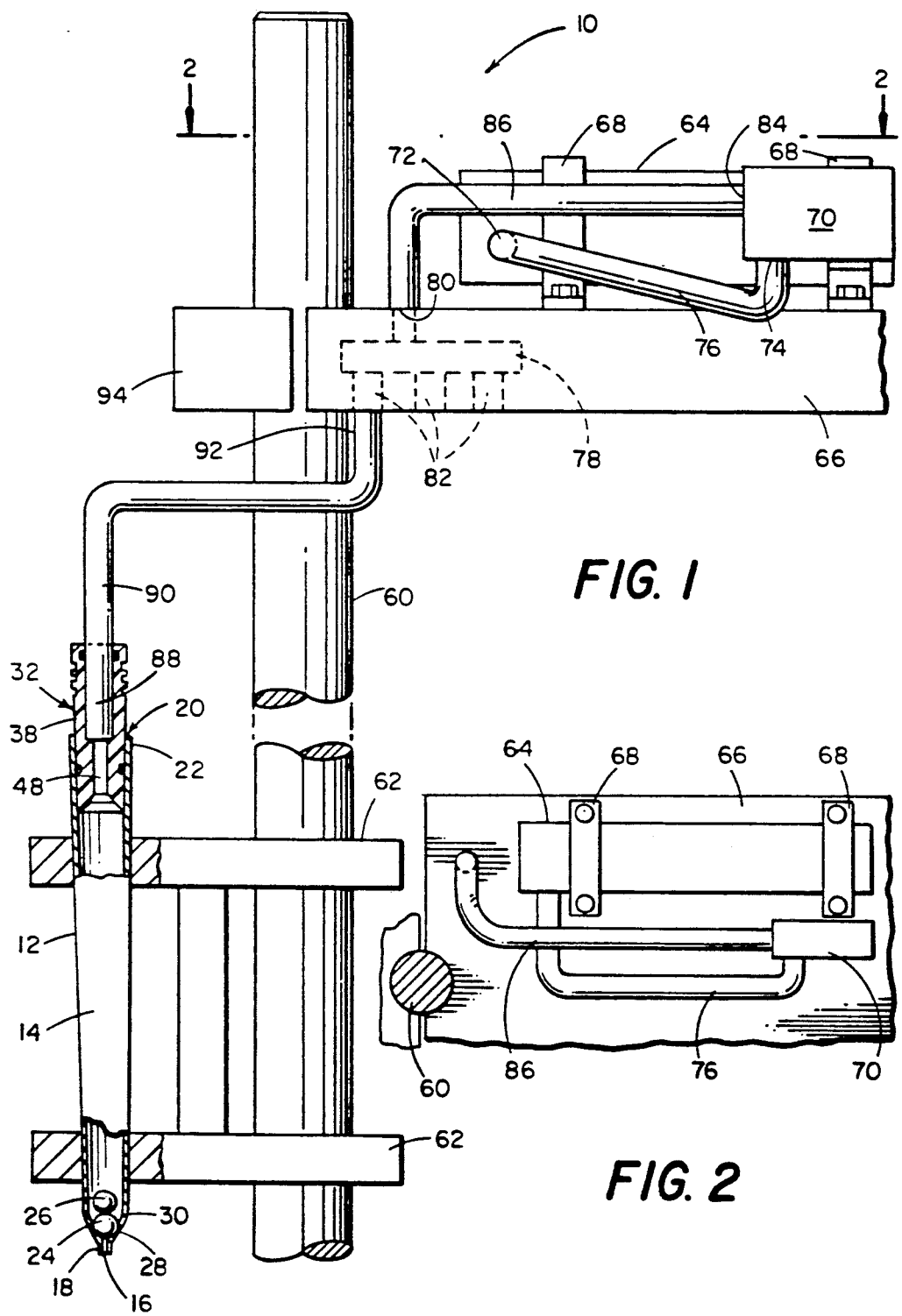
FIG. 1 is a side elevational, fragmentary cross sectional view of a liquid sampler according to the invention.
FIG. 2 is a top view of the sampling device taken on line 2—2 of FIG. 1 and showing details of the air cylinder, toggle valve, and connecting hoses.

This invention relates to a device and a method for sampling a liquid. The device comprises a pipet having a first and a second sealing member disposed in a chamber therein. The sealing members are freely movable within the chamber. The first sealing member has a specific gravity greater than, and the second sealing member has a specific gravity less than, the specific gravity of the liquid. Prior to positioning the pipet in the liquid, the first sealing member is seated on a first seat disposed between a first opening and the chamber by introducing a gas into the chamber through a second opening, to prevent liquid from entering the chamber. After positioning the device so that the first opening is at a predetermined depth in the body of liquid to be sampled, sufficient gas is removed from the chamber to unseat the first sealing member and allow liquid into the chamber through the first opening. Sufficient liquid is allowed to enter the chamber to seat the second sealing member on a second seat disposed between the second opening and the chamber. Gas is then introduced to the chamber through the second opening to pressurize the chamber and maintain the first sealing member seated to contain the sample in the chamber, and which with lower pressure outside the chamber maintains the second sealing member seated as well if the pipet is maintained substantially upright.

The operator may vary the rate of drawing the sample and the volume of sample obtained. For instance, the operator may remove an amount of gas from the chamber just sufficient to allow the chamber to partially fill, and then the operator may pressurize the chamber to reseat the first sealing member. Variations on such a method can be applied, such as intermittent such fill and stop operations, or, in another embodiment, by removing gas from the chamber at a slow, continuous rate to achieve a slow, continuous filling of the chamber.

This invention provides many benefits and overcomes difficulties and shortcomings in the prior art. This invention does not require visual monitoring and direct handling while taking a sample; thereby facilitating drawing submersed samples and samples of hazardous liquids. The sealing members and other components can be constructed of corrosion resistant materials such as stainless steel and polypropylene rather than elastomeric materials such as rubber. The method and apparatus of the invention can be used in sampling liquids such as two-phase systems that require minimal disturbing of the sampled liquid, so that a substantially representative sample can be obtained without significant settling occurring. Samples can be accurately and timely drawn at operator selected depths with a minimum or absence of leakage of the sampled liquid out of the sampling device.

The invention also provides for drawing multiple samples of liquid concurrently by one operator or in one operation. Accordingly, in one embodiment described herein, the device comprises a plurality of pipets and has a unitary design convenient for taking such multiple samples and for obtaining liquid samples in a substantially light-free environment such as in photographic manufacturing processes. Multiple samples may be obtained at predetermined depths in a stratified or in a homogeneous liquid to indicate, for example, whether the liquid is well-mixed. The operator may obtain samples by partially filling the chamber, or by partially filling the chamber, then stopping, and then filling, which procedure can be repeated as the operator may wish. Slow, continuous samples may be obtained. Accordingly, the device and method of this invention can be employed where it is desired to obtain single or multiple samples of a liquid, and intermittent or continuous samples, for the above-described applications. Examples of such applications are the preparation of foods, the manufacture of pharmaceuticals, and photographic products manufacturing.

The method and device of the present invention can also be used in drawing liquid samples in applications in which it is desired to limit operator contact with the liquid and where it is infeasible or undesirable to directly and visually monitor the sampling process. The invention can also be used in sampling corrosive liquids that materials such as rubber and the like used in prior art sampling devices cannot withstand.

DESCRIPTION OF PREFERRED EMBODIMENTS

In one embodiment, the device for sampling a liquid comprises a pipet having a chamber therein. The pipet has a first end having a first opening therethrough communicating with the chamber for introducing the liquid from outside the device into the chamber, and the pipet has a second end having a second opening therethrough communicating with the chamber for introducing or removing a gas respectively to or from the chamber. A freely movable first sealing member having a specific gravity greater than the specific gravity of the liquid and a freely movable second sealing member having a specific gravity less than the specific gravity of the liquid are positioned in the chamber. A first seat is disposed between the first opening and the chamber for substantially seating the first sealing member thereon so as to substantially contain a sample of the liquid within the chamber. A second seat is disposed between the second opening and the chamber for substantially seating the second sealing member thereon so as to substantially stop further flow of the liquid into the chamber.

In a preferred embodiment, the first sealing member is substantially rigid and has a first spherical surface. The second sealing member is substantially rigid and has a second spherical surface. The first seat is spherical for substantially seating thereon the first sealing member by the first spherical surface so as to substantially contain a sample of the liquid within the chamber.

In another preferred embodiment, the first and second sealing members each comprises a ball. A preferred liquid sampling device further comprises means for introducing or removing a gas respectively to or from the chamber, and preferred means for introducing or removing a gas comprises an air cylinder. A preferred sampling device comprises a plurality of pipets, and further comprises (a) a manifold having (i) an inlet port in communication with means for introducing or removing a gas and (ii) an outlet port in communication with each such first opening of each pipet, and (b) valve means positioned between the manifold and the means for introducing or removing a gas and in communication each therewith to control the introduction or removal of gas therebetween, whereby liquid can be drawn concurrently into each of the pipets and each sample substantially contained within each such chamber.

A preferred relative position of the first and second sealing members within the chamber is such that the first sealing member maintains a relative position between the second sealing member and the first seat.

Figures 3, 4:
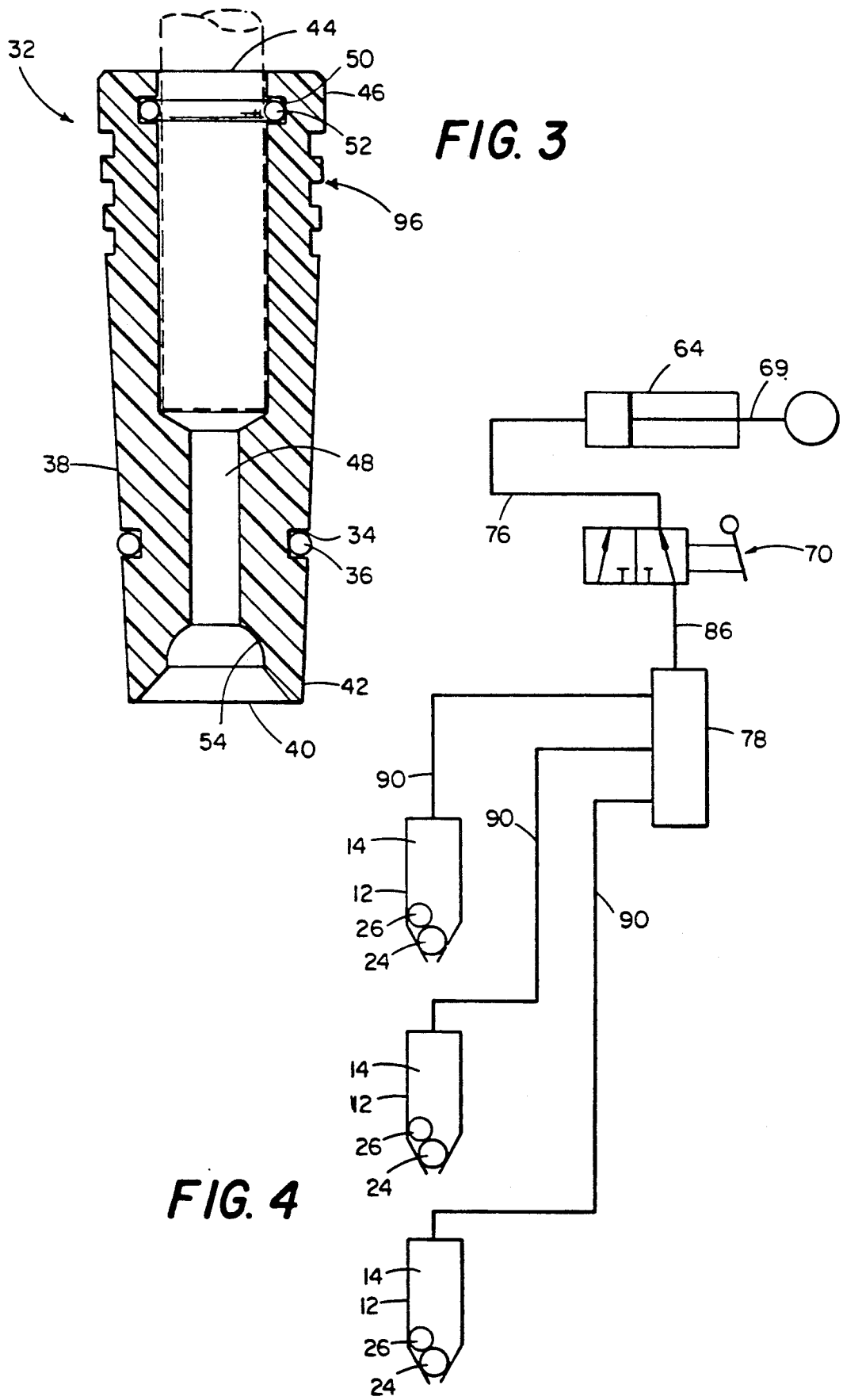
FIG. 3 is an enlarged cross sectional view of a stopper according to the invention.
FIG. 4 is a system diagram illustrating the invention as configured for drawing multiple samples concurrently.

A preferred embodiment of a liquid sampling device 10, according to the present invention, is shown in FIGS. 1-3. From the drawings and the following description, the unitary design of sampling device 10 will become apparent.

Provided is a pipet-like device, hereinafter termed "pipet", 12, that as shown in FIG. 1 comprises an interior chamber 14, a first opening 16 at a first end 18, and a second opening 20 at a second end 22. Pipet 12 as shown therein has a circular cross section, and tapers from about a 0.5 inch (13 mm) inner diameter at second opening 20, to about a 0.35 inch (9 mm) inner diameter above first opening 16, then to a smaller dimension for first opening 16. The size, location and configuration of first opening 16 and second opening 18 may vary and are readily selectable by the operator. For example, either opening can be positioned in a side wall of pipet 12, can be of a convenient size for the operator or application, and have other than a circular configuration.

Positioned within chamber 14 is freely movable first ball sealing member 24 and freely movable second ball sealing member 26. First seat 28 is disposed on inner wall 30 near first end 18 of pipet 12 for seating first ball member 24. Stopper 32 is positioned in opening 20 to snuggly fit within chamber 14. Stopper 32 has a recess 34 having a circular cross section for snuggly positioning therein O-ring 36. O-ring 36 has a diameter larger than the width of recess 34 to compressibly secure stopper 32 in chamber 14 and to also substantially prevent the flow of liquid out of the chamber between inner wall 30 and outer surface 38 of stopper 32. Stopper 32 has a first opening 40 at a first end 42, a second opening 44 at a second end 46, and a passage 48 therethrough between opening 40 and opening 44. Passage 48 has a recess 50 having a circular cross section for snuggly positioning therein O-ring 52. Second seat 54 is disposed at end 42 of stopper 32 and is spherical for seating second ball member 26. Second ball member 26 is made of a suitable material to have a specific gravity less than the specific gravity of the liquid to be sampled such that, when chamber 14 is filled with a liquid, second ball member 26 can float on the liquid and seat on second seat 54. First ball member 24 is made of a suitable material to have a specific gravity greater than the specific gravity of the liquid to be sampled, so that first ball member 24 can seat on first seat 28.

The diameters and relative positions in chamber 14 of first ball member 24 and second ball member 26 must be such as to permit free movement of each ball member within chamber 14 and allow each ball member to seat on its respective seat as above described. In the preferred embodiment described herein, first ball member 24 has a diameter of about 0.25 inches (0.64 cm), and second ball member 26 has a diameter of about 0.24 inches (0.60 cm). One skilled in the art can readily select dimensions for ball members 24 and 26 and pipet 12 that will work as above-described. For example, each ball member can have a diameter less than the inner diameter of pipet 12 but at least one-half of the largest such inner diameter of pipet 12 to ensure that the relative orientation of the ball members within and with respect to chamber 14 will not change. In other words, first ball member 24 can maintain a relative position between second ball member 26 and first seat 28 before, during, and after the below-described steps or operations when using the liquid sampler 10 in the practice of the invention.

The surface of first seat 28 should conform to the seating surface of first ball member 24, in order to maximize the seating area and minimize leakage of liquid out of chamber 14. By "seating surface" is meant the surface portion of a sealing member that contacts a seat when the sealing member is seated. First ball member 24 can be shaped so that just the seating surface conforms to first seat 28, and the shape of nonseating portions is not material. It is preferred that first seat 28 and the seating surface of first ball member 24 are annular, and in the embodiment described herein first seat 28 and first ball member 24 are spherical. In the preferred embodiment, pipet 12 is polypropylene and inner wall 30 is softened near first end 18 by heating, after which at such location first ball member 24 is pressed against inner wall 30 while inner wall 30 is allowed to cool. Seat 28 thus formed substantially defines a spherical surface and provides a greater seating surface area than would line surface contact between first ball member 24 and seat 28, thus improving the resistance to leakage of liquid from chamber 14 through seat 28.

Pipet 12 is mounted to rod 60 by mounting brackets 62. Means for introducing or removing a gas comprises air cylinder 64 mounted on plate 66 by mounting brackets 68. Air cylinder 64 can be operable by any convenient means, for example, as by pneumatic control means. In the embodiment having the unitary design as described herein, a hand-operated plunger 69 shown schematically in FIG. 4 is provided for operating the actuator of air cylinder 64, which design facilitates the handling, carrying, use, and transfer of sampling device 10 by the operator. Plunger 69 also comprises means for controlling the rate and volume of gas introduction or removal respectively to or from chamber 14. The operator by controlling the rate of movement and the position of plunger 69 can thereby partially fill chamber 14 at an operator-selected rate, then stop, and have the option of drawing more liquid into chamber 14 at a later time, as with intermittent sampling. Alternatively, the operator can draw a continuous sample at an operator-selected rate to partially or completely fill chamber 14. Means for controlling the rate and volume of gas introduction or removal respectively to or from the chamber can also comprise automatic or programmable-controller controlled gas cylinders and the like.

Valve means, for example, toggle valve 70 as shown in FIGS. 1, 2 and 4, is provided to control the introduction or removal of air between air cylinder 64 and pipet 12. In the embodiment described herein, toggle valve 70 is mounted on one end of air cylinder 64. Outlet port 72 of air cylinder 64 is connected to inlet port 74 of toggle valve 70 by hose 76. Plate 66 has manifold 78, shown in phantom in FIG. 1 and schematically in FIG. 4, therein, having an inlet port 80 and three outlet ports 82. Outlet port 84 of toggle valve 70 is connected to manifold inlet port 80 by hose 86. As shown in FIG. 4, toggle valve 70 is thus connected in series to allow an operator to selectively open or close communication between air cylinder 64 and manifold 78. A first end 88 of air hose 90 is snuggly positioned in passage 48, as shown in FIG. 1. O-ring 52 has a diameter greater than the width of recess 50 to compressibly secure end 88 of hose 90 in passage 48. A second end 92 of hose 90 is secured to a manifold outlet port 82 by air-tight fastening means (not shown). Plate 66 is mounted by mounting bracket 94 on rod 60. Liquid sampling device 10 as so described thus defines a unitary device, or in other words, a device in which the relative positions and orientations of structural components so described can be maintained.

In sampling a corrosive liquid, for example a photographic emulsion, it is preferred that the materials of device 10 are substantially nonreactive and corrosion resistant, in order that the emulsion and the samples are substantially uncontaminated. For example, in one embodiment stopper 32 and first ball member 24 can each comprise 316 Stainless Steel. Pipet 12, second ball member 26, and hoses 90 can comprise clear polypropylene. Rod 60 and mounting brackets 62 can comprise PVC.

The selection of materials for the ball members is also made in view of the above-described relative specific gravities. In one embodiment, in sampling a photographic emulsion having a specific gravity in the range from about 0.95 to about 1.05, first ball member 24 can be 316 Stainless Steel having a specific gravity of about 8.0, and second ball member 26 can be polypropylene having a specific gravity of about 0.90.

In one embodiment, the method of the present invention in sampling liquids at a predetermined depth within the body of a liquid to be sampled, and with a liquid sampling device of the invention, comprises the steps of (a) sufficiently pressurizing the chamber with a gas introduced by the means for introducing or removing a gas through the second opening so as to substantially seat the first sealing member on the first seat; (b) positioning the device so that the first opening of the pipet is at the predetermined depth within the body of the liquid; (c) sufficiently depressurizing the chamber by removing at least some of the gas from the chamber with the means for introducing or removing a gas to substantially unseat the first sealing member to allow liquid to enter the chamber to obtain the sample; (d) allowing sufficient liquid to enter the chamber to seat the second sealing member on the second seat so as to substantially stop flow of the liquid into the chamber; and (e) sufficiently pressurizing the chamber to reseat the first sealing member on the first seat so as to substantially contain the sample within the chamber. In a preferred embodiment, the method of the invention further comprises the step of disconnecting the means for introducing and removing a gas so that the gas pressure outside the chamber is less than the gas pressure within the chamber to maintain the second sealing member seated on the second seat, thereby minimizing or stopping leakage of the sample from the chamber through the second seat.

In a preferred embodiment, the method of the invention of obtaining samples of a liquid at predetermined depths within the body of a liquid to be sampled, and with a liquid sampling device comprising (a) a plurality of pipets, each such pipet being positioned at a predetermined depth, and each such pipet comprising a chamber, a first end having a first opening therethrough communicating with the chamber, and a second end having a second opening therethrough communicating with the chamber, (b) a freely movable first sealing member having a specific gravity greater than the specific gravity of the liquid positioned in each such chamber, (c) a freely movable second sealing member having a specific gravity less than the specific gravity of said liquid positioned in each such chamber, (d) a first seat disposed between each first opening and each chamber for substantially seating each respective first sealing member thereon, (e) a second seat disposed between each second opening and each chamber for substantially seating each respective second sealing member thereon, and (f) means for introducing or removing a gas respectively to or from each chamber, comprises the steps of:

(a) sufficiently pressurizing each chamber with a gas introduced by the means for introducing or removing a gas through each second opening so as to substantially seat each first sealing member on each respective first seat;

(b) positioning said device so that each first opening of each pipet is at one of the predetermined depths within the body of the liquid;

(c) sufficiently depressurizing each chamber by removing at least some of the gas from each chamber with the means for introducing or removing a gas to substantially unseat each first sealing member to allow liquid to enter each respective chamber to obtain each sample;

(d) allowing sufficient liquid to enter each chamber to seat each respective second sealing member on each respective second seat so as to substantially stop flow of the liquid into each chamber; and (e) sufficiently pressurizing each chamber to reseat each respective first sealing member on each respective first seat so as to substantially contain each sample within each chamber.

The method of the invention can be practiced both in applications in which the liquid that is sampled is stratified and in those in which the liquid is homogeneous. The method of the invention may be practiced by positioning liquid sampler 10 in a container holding liquid to be sampled after the liquid level in the container has been established at the desired level. Liquid sampler 10 may also be positioned in a container that is empty or partially filled, and liquid then added to the container to a level enabling the operator to obtain a sample at a predetermined depth.

Another embodiment of the method of the invention comprises controlling the rate and volume of gas introduction or removal respectively to or from the chamber, thereby allowing the drawing of a partial sample, an intermittent sample, or a continuous sample, and allowing a variable sampling rate.

The operation of the liquid sampling device 10 will be described with reference to FIGS. 1, 2, and 4 in accordance with a method of obtaining a sample of a photographic film emulsion in a liquid, that is non-gelled, state; however, the liquid sampling device can be used in any suitable liquid sampling application. In accordance with the method of the present invention, a sampling device is configured as shown schematically in FIG. 3 such that three sampling pipets 12 are each mounted on rod 60 by mounting brackets 62. Each pipet 12 is connected as above-described by a hose 90 from each respective stopper 32 to a manifold outlet port 82.

With toggle valve 70 open, plunger 69 of air cylinder 64 is depressed to force air through manifold 78 and sufficiently pressurize each chamber 14 so as to seat each ball member 24 on each respective seat 28. Toggle valve 70 is then closed to substantially maintain pressure in each chamber 14. Liquid sampler 10 is then positioned in a kettle containing liquid photographic emulsion (not illustrated) by a locating fixture (not illustrated) so as to immerse the portion of rod 60 upon which are mounted pipets 12 to position each pipet 12 at a predetermined depth in the body of the liquid, while leaving plate 66 not immersed and toggle valve 70 readily accessible by the operator.

Toggle valve 70 is then opened and plunger 69 is retracted so that each chamber 14 is sufficiently depressurized such that hydrostatic pressure substantially unseats each ball member 24. Liquid emulsion thus enters each chamber 14, thereby obtaining the samples. Sufficient liquid is allowed to enter each chamber 14 to seat each ball member 26 on each respective seat 54 so as to substantially stop flow of liquid into each chamber 14. Alternatively, a partial sample may be obtained in each pipet 12 as above-described if the operator so chooses.

The actuator of air cylinder 64 is then positioned by depressing plunger 69 to sufficiently pressurize each chamber 14 to reseat each ball member 24 on each respective seat 28 so as to substantially contain each liquid sample within each chamber 14, and toggle valve 70 is then closed to substantially maintain the air pressure in each chamber 14. Liquid sampler 10 may then be removed from the kettle and the pipets 12 taken, either still mounted to rod 60 or after being removed from rod 60, to a laboratory for analysis.

In the preferred practice of the invention, after removing pipets 12 from the emulsion, each hose 90 is disconnected from each pipet 12 or from each outlet 82 so that the air pressure outside each chamber 14 is atmospheric pressure and is less than the pressure inside each chamber 14. Such a step helps maintain ball member 26 seated on seat 54 and minimizes or stops leakage of the sample from chamber 14 through seat 54 such as when pipet 12 is being handled. For example, pipet 12 can be removed from device 10 for subsequent testing on the contained sample, and so long as pipet 12 is maintained substantially in an upright position, ball member 26 can maintain its seating on seat 54 to prevent leakage of the sample out of pipet 12.

The sampling device and method of sampling of the invention are useful in sampling a photographic film emulsion made during the manufacturing process. Accordingly, the invention is capable of being practiced in a substantially dark environment as is required in such manufacturing processes. The operator can readily position sampling device 10 by virtue of its unitary design in a kettle containing photographic emulsion by resting the bottom of plate 66 on top of a side wall of the kettle with pipet 12 immersed in the emulsion and secure it to the kettle by any convenient securing means (not illustrated). Such procedure can readily be conducted in the substantially light-free environment, and registers 96 are provided on pipet 12 for tactile identification by the operator in the dark. Therefore, when multiple samples are concurrently drawn from different depths as above-described, each pipet 12 can have registers 96, shown in FIGS. 1 and 3, each such registers 96 having a different configuration and thus capable of being distinguished tactilely in the dark. This enables the operator to track each sample drawn with each corresponding predetermined depth, thus facilitating carrying out any desired tests or procedures on each sample without having to visually tell each pipet apart.

The invention has been described in detail with particular reference to a preferred embodiment thereof, but it will be understood that variations and modifications can be effected within the spirit and scope of the invention.

We claim:

1. A device for sampling a liquid, comprising:
   a pipet having a chamber therein, said pipet having a first end having a first opening therethrough, said first opening communicating with said chamber for introducing said liquid from outside said device into said chamber, said pipet additionally having a second end having a second opening therethrough, said second opening communicating with said chamber for introducing or removing a gas respectively to or from said chamber;
   a freely movable first sealing member in said chamber, said first sealing member having a specific gravity greater than the specific gravity of said liquid;
   a freely movable second sealing member in said chamber, said second sealing member having a specific gravity less than the specific gravity of said liquid;
   first seat means disposed between said first opening and said chamber for seating said first sealing member thereon so as to contain a sample of said liquid within said chamber; and
   second seat means, disposed between said second opening and said chamber, for seating said second sealing member thereon so as to stop further flow of said liquid into said chamber through said first opening, and for thereafter permitting the unseating of said second sealing member upon the controlled introduction of a gas to said chamber through said second opening whereby said second sealing member releases from sealing engagement with said second seat means.

2. The device of claim 1, wherein:
   said first sealing member is rigid and has a first spherical surface;
   said second sealing member is rigid and has a second spherical surface;
   said first seat means is a spherical first seat for seating thereon said first sealing member by said first spherical surface so as to contain said sample within said chamber; and
   said second seat means is a spherical second seat for seating thereon said second sealing member by said second spherical surface upon the introduction of sufficient liquid into said chamber to fill said chamber thereby stopping further flow of liquid therein and for thereafter permitting the unseating of said second sealing member upon the controlled introduction of a gas to said chamber through said second opening whereby said second sealing member can release from sealing engagement with said second seat.

3. The device of claim 1, wherein said first and second sealing members each comprises a ball.

4. The device of claim 1, further comprising:
   means for introducing or removing a gas respectively to or from said chamber;
   means for controlling the rate and volume of gas introduction or removal respectively to or from said chamber; and
   a hose connecting said means for introducing or removing a gas via said second opening of said pipette whereby said means for introducing and removing a gas is capable of being operated from a position remote from said liquid being sampled.

5. The device of claim 4, wherein said means for introducing or removing a gas comprises an air cylinder.

6. The device of claim 1, wherein the relative position of said first and said second sealing members within the chamber is such that said first sealing member maintains a relative position between said second sealing member and said first seat.

7. The device of claim 1, wherein said device comprises a plurality of said pipets, and further comprising (a) a manifold having (i) an inlet port in communication with said means for introducing or removing a gas, and (ii) an outlet port in communication with each said first opening of each said pipet, and (b) valve means positioned between said manifold and said means for introducing or removing a gas and in communication each therewith to control the introduction or removal of gas therebetween, whereby liquid can be drawn concurrently into each of said pipets and each said sample contained within each said chamber.

8. A method of obtaining a sample of a liquid at a predetermined depth within the body of a liquid to be sampled, and with a liquid sampling device comprising (a) a pipet comprising a chamber, a first end having a first opening therethrough communicating with said chamber, and a second end having a second opening therethrough communicating with said chamber, (b) a freely movable first sealing member having a specific gravity greater than the specific gravity of said liquid positioned in said chamber, (c) a freely movable second sealing member having a specific gravity less than the specific gravity of said liquid positioned in said chamber, (d) a first seat disposed between said first opening and said chamber for seating said first sealing member thereon, (e) a second seat disposed between said second opening and said chamber for seating said second sealing member thereon, and (f) means for introducing or removing a gas respectively to or from said chamber, comprising the steps of:

(a) pressurizing said chamber with a gas introduced by said means for introducing or removing a gas through said second opening so as to seat said first sealing member on said first seat;

(b) positioning said device so that said first opening of said pipet is at said predetermined depth within said body of said liquid;

(c) depressurizing said chamber by removing at least some of said gas from said chamber with said means for introducing or removing a gas to unseat said first sealing member to allow liquid to enter said chamber to obtain said sample;

(d) allowing sufficient liquid to enter into and fill said chamber to seat said second sealing member on said second seat so as to substantially stop flow of said liquid into said chamber; and (e) pressurizing said chamber to reseat said first sealing member on said first seat so as to contain said sample within said chamber.

9. The method of claim 8, further comprising the step of disconnecting said means for introducing and removing a gas so that the gas pressure outside said chamber is less than the gas pressure within said chamber to maintain said second sealing member seated on said second seat, thereby minimizing or stopping leakage of said sample from said chamber through said second seat.

10. A method of obtaining samples of a liquid at predetermined depths within the body of a liquid to be sampled, and with a liquid sampling device comprising (a) a plurality of pipets, each said pipet being positioned at a predetermined depth, and each said pipet comprising a chamber, a first end having a first opening therethrough communicating with said chamber, and a second end having a second opening therethrough communicating with said chamber, (b) a freely movable first sealing member having a specific gravity greater than the specific gravity of said liquid positioned in each said chamber, (c) a freely movable second sealing member having a specific gravity less than the specific gravity of said liquid positioned in each said chamber, (d) a first seat disposed between each said first opening and each said chamber for seating each respective said first sealing member thereon, (e) a second seat disposed between each said second opening and each said chamber for seating each respective said second sealing member thereon, and (f) means for introducing or removing a gas respectively to or from each said chamber, comprising the steps of:

(a) pressurizing each said chamber with a gas introduced by said means for introducing or removing a gas through each said second opening so as to seat each said first sealing member on each respective said first seat;

(b) positioning said device so that each said first opening of each said pipet is at one of said predetermined depths within said body of said liquid;

(c) depressurizing each said chamber by removing at least some of said gas from each said chamber with said means for introducing or removing a gas to unseat each said first sealing member to allow liquid to enter each respective said chamber to obtain each said sample;

(d) allowing sufficient liquid to enter into and fill each said chamber to seat each respective said second sealing member on each respective said second seat so as to stop flow of said liquid into each said chamber; and (e) pressurizing each said chamber to reseat each respective said first sealing member on each respective said first seat so as to contain each said sample within each said chamber.

11. The method of claim 10, wherein said liquid that is sampled is stratified.

12. The method of claim 10, wherein said liquid that is sampled is homogeneous.

13. The method of claim 10, wherein said device further comprises means for controlling the rate and volume of gas introduction or removal respectively to or from said chamber, and further comprising the step of controlling the rate and volume of gas introduction or removal respectively to or from said chamber, thereby allowing the drawing of a partial sample, an intermittent sample, or a continuous sample, and allowing a variable sampling rate.

* * * * *